(12) United States Patent
Kim et al.

(10) Patent No.: US 11,684,301 B1
(45) Date of Patent: Jun. 27, 2023

(54) METHODS, SYSTEMS, AND NON-TRANSITORY COMPUTER-READABLE MEDIUMS FOR SSVEP DETECTION

(71) Applicant: Toyota Motor Engineering & Manufacturing North America, Inc., Plano, TX (US)

(72) Inventors: Insoo Kim, Avon, CT (US); Hossein Hamidi Shishavan, New Britain, CT (US); Kia Golzari, Vernon, CT (US); Muhamed Farooq, Ann Arbor, MI (US)

(73) Assignees: TOYOTA MOTOR ENGINEERING & MANUFACTURING NORTH AMERICA, INC., Plano, TX (US); UNIVERSITY OF CONNECTICUT HEALTH CENTER, Farmington, CT (US)

( * ) Notice: Subject to any disclaimer, the term of this patent is extended or adjusted under 35 U.S.C. 154(b) by 0 days.

(21) Appl. No.: 17/576,370

(22) Filed: Jan. 14, 2022

(51) Int. Cl.
| | |
|---|---|
| *G08B 23/00* | (2006.01) |
| *A61B 5/18* | (2006.01) |
| *B60W 40/08* | (2012.01) |

(52) U.S. Cl.
CPC .............. *A61B 5/18* (2013.01); *B60W 40/08* (2013.01); *B60W 2040/0872* (2013.01); *B60W 2540/22* (2013.01); *B60W 2540/221* (2020.02)

(58) Field of Classification Search
CPC ... A61B 5/18; B60W 40/08; B60W 2540/221; B60W 2040/0872; B60W 2540/22
(Continued)

(56) References Cited

U.S. PATENT DOCUMENTS

2014/0371603 A1* 12/2014 Fujita ................. A61B 5/18
600/479
2021/0163033 A1* 6/2021 Kang ................. B60W 40/08
(Continued)

FOREIGN PATENT DOCUMENTS

| CN | 105929937 A | 9/2016 |
|---|---|---|
| CN | 107483992 A | 12/2017 |

(Continued)

OTHER PUBLICATIONS

SSVEP-based experimental procedure for brain-robot interaction with humanoid robots (https://www.ncbi.nlm.nih.gov/pmc/articles/PMC4692746/pdf/jove-105-53558.pdf), Nov. 24, 2015.
(Continued)

*Primary Examiner* — Naomi J Small
(74) *Attorney, Agent, or Firm* — Dinsmore & Shohl LLP (57) ABSTRACT

In accordance with one embodiment of the present disclosure, a method includes generating a plurality of icons, wherein each icon has a target frequency unique from each other, receiving brain activity data based on an epoch, generating a reference signal based on the epoch, calculating correlation coefficients between the brain activity data and the reference signal, wherein the correlation coefficients are calculated in a window that is within ±0.5 Hz of the target frequencies, including endpoints, determining a confidence score based on the correlation coefficients and the epoch, and determining a selected icon among the plurality of icons based on the correlation coefficients in response to the confidence score surpassing a threshold confidence score.

20 Claims, 6 Drawing Sheets

(58) Field of Classification Search
USPC .......................................................... 340/576
See application file for complete search history.

(56) References Cited

U.S. PATENT DOCUMENTS

2022/0322994 A1* 10/2022 Farooq ................... A61B 5/112
2022/0334641 A1* 10/2022 Farooq ................... G06F 3/015

FOREIGN PATENT DOCUMENTS

| | | |
|---|---|---|
| CN | 109471530 A | 3/2019 |
| CN | 106951064 B | 5/2019 |
| CN | 107390873 B | 3/2020 |
| CN | 110956701 A | 4/2020 |
| CN | 111399652 A | 7/2020 |
| KR | 2143920 B1 | 8/2020 |

OTHER PUBLICATIONS

SSVEP enhancement based on canonical correlation analysis to improve BCI performances (https://hal.archives-ouvertes.fr/hal-01352059/document). Aug. 5, 2016.
Optimizing the use of SSVEP-based brain-computer interfaces for human-computer interaction (http://tel.archives-ouvertes.fr/tel-01476185/document), Feb. 24, 2017.

* cited by examiner

METHODS, SYSTEMS, AND NON-TRANSITORY COMPUTER-READABLE MEDIUMS FOR SSVEP DETECTION

TECHNICAL FIELD

The present disclosure relates to brain-computer interfaces (BCI), and more particularly to the optimization of SSVEP detection in BCIs.

BACKGROUND

A BCE is a type of human-computer interaction that connects the brain to external electronic devices. One of the most effective methods for connecting the brain to an external electronic device is through the evocation and analysis of steady-state visually evoked potentials (SSVEP). SSVEP is brain activity that is a natural response to visual stimulation at specific frequencies. When the eye views a visual stimulus (e.g., an icon) flickering at a rate ranging from 3.5 Hz to 75 Hz, for example, the brain generates electrical activity at the same or multiples (i.e., harmonic frequencies) of the frequency of the visual stimulus. SSVEP-based BCI systems may utilize user interfaces having a plurality of icons for the user to interact with. Each icon may be flickering at a different frequency to evoke particular brain activity when viewed by a user. The brain activity may be correlated to the flicker frequency which may be further correlated to an interaction with an icon.

Current SSVEP-based BCI systems may utilize canonical correlation analysis (CCA). CCA calculates the correlation coefficients between two datasets: the acquired brain activity (e.g., EEG) data from the BCI user and a synthetically generated sine-cosine reference signal. Target frequencies are identified based on the correlation coefficients between the two datasets for each frequency of the reference signal. While this process is useful for visualizing the CCA coefficients across the frequency range of the reference signal, it is time-consuming and utilizes significant computational resources. Therefore, efficient strategies for SSVEP detection that can identify a target frequency in less time and with fewer resources are desired.

SUMMARY

In accordance with one embodiment of the present disclosure, a method includes generating a plurality of icons, wherein each icon has a target frequency unique from each other, receiving brain activity data based on an epoch, generating a reference signal based on the epoch, calculating correlation coefficients between the brain activity data and the reference signal, wherein the correlation coefficients are calculated in a window that is within ±0.5 Hz of the target frequencies, including endpoints, determining a confidence score based on the correlation coefficients and the epoch, and determining a selected icon among the plurality of icons based on the correlation coefficients in response to the confidence score surpassing a threshold confidence score.

In accordance with another embodiment of the present disclosure, a system includes a processor, an electronic display, a brain activity sensor, and a memory module. The memory module has machine-readable instructions that, when executed by the processor, cause the processor to perform operations including generating a plurality of icons, wherein each icon has a target frequency unique from each other, receiving brain activity data based on an epoch, generating a reference signal based on the epoch, calculating correlation coefficients between the brain activity data and the reference signal, wherein the correlation coefficients are calculated in a window that is within ±0.5 Hz of the target frequencies, including endpoints, determining a confidence score based on the correlation coefficients and the epoch, and determining a selected icon among the plurality of icons based on the correlation coefficients in response to the confidence score surpassing a threshold confidence score.

In accordance with yet another embodiment of the present disclosure, a non-transitory computer-readable medium has machine-readable instructions that, when executed by a processor, cause the processor to perform operations including generating a plurality of icons, wherein each icon has a target frequency unique from each other, receiving brain activity data based on an epoch, generating a reference signal based on the epoch, calculating correlation coefficients between the brain activity data and the reference signal, wherein the correlation coefficients are calculated in a window that is within ±0.5 Hz of the target frequencies, including endpoints, determining a confidence score based on the correlation coefficients and the epoch, and determining a selected icon among the plurality of icons based on the correlation coefficients in response to the confidence score surpassing a threshold confidence score.

Although the concepts of the present disclosure are described herein with primary reference to automobiles, it is contemplated that the concepts will enjoy applicability to any electronic display having a user interface. For example, and not by way of limitation, it is contemplated that the concepts of the present disclosure will enjoy applicability to personal computers.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

The embodiments disclosed herein include methods, systems, and non-transitory computer-readable mediums having machine-readable instructions for SSVEP detection. In embodiments disclosed herein, an SSVEP-based BCI may utilize an electronic display to present a user interface to a user. The user interface may have a plurality of flickering icons that invoke brain activity in a user when the user views an icon. An SSVEP-based BCI may utilize canonical correlation analysis to determine the icon the user is viewing. CCA calculates the correlation coefficients between two datasets: the acquired brain activity (e.g., EEG) data from the BCI user and a synthetically generated sine-cosine reference signal. Target frequencies are identified based on the correlation coefficients between the two datasets for each frequency of the reference signal.

In standard CCA calculations, the range of the reference signal frequency is predetermined to encompass the flickering frequencies for visual stimulation. A step size is also defined to calculate the reference signal wherein the resolution is equal to the step size. For example, if the step size is 0.01, then the reference signal will be calculated from the minimum frequency to the maximum frequency with 0.01 increments. However, this is time-consuming and utilizes significant computational resources.

In embodiments disclosed here, systems enhance the efficiency of CCA analysis in SSVEP-based BCIs by narrowing the analysis to the target frequencies as well as a window of ±0.5 Hz to account for imprecisions that naturally occur in the SSVEP paradigm. In addition, embodiments determine a confidence level and compare the confidence level to a predetermined threshold after a predetermined number of epochs to improve execution time.

Figure 1:
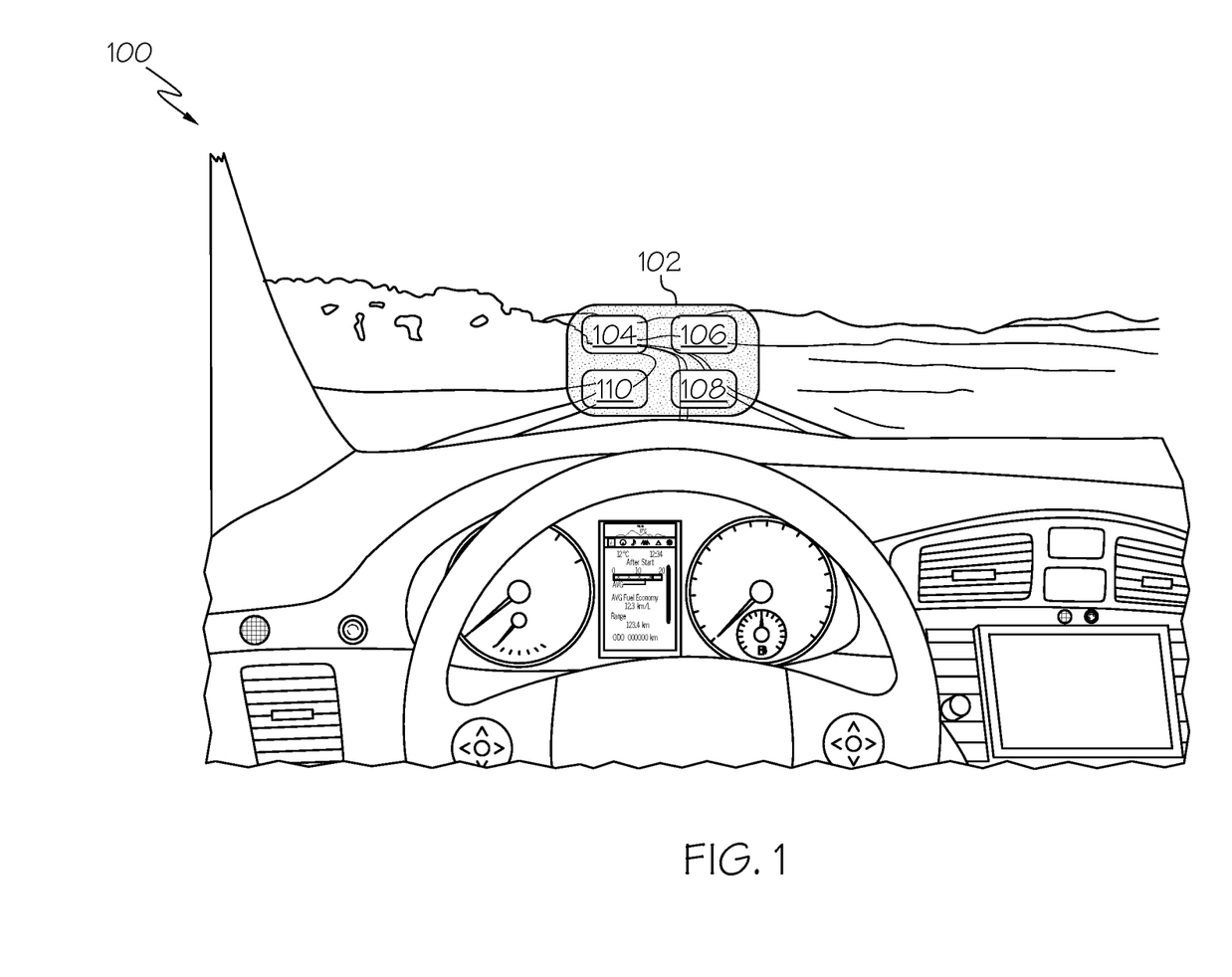
FIG. 1 depicts an illustrative scenario of a user viewing a heads-up display having an SSVEP-based BCI, according to one or more embodiments shown and described herein.

Referring now to FIG. 1, a scenario 100 of a user viewing a HUD 102 having an SSVEP-based BCI is depicted. The HUD 102 may be an electronic display having a level of transparency. For example, the HUD 102 may be partially or fully transparent. Presented on the HUD 102 may be a user interface. The user interface may comprise a plurality of icons 104, 106, 108, 110. Each icon of the icons 104, 106, 108, 110 may flicker at a rate different from the other icons. The rate at which an icon flickers reflects the type and/or amount of brain activity that is evoked from the user when the user focuses on the icon. For example, if an icon flickers at 6.67 Hz, then the brain activity may be elevated at 6.67 Hz and at multiples thereof referred to as "harmonic frequencies."

In some embodiments, the user interface may also have display parameter settings. The user interface may have a particular arrangement for the icons 104, 106, 108, 110 that may affect the type and/or amount of brain activity that is evoked from the user. For example, in scenario 100, the icons 104, 106, 108, 110 are in a 2×2 arrangement. The user interface may also have a particular color for the icons 104, 106, 108, 110 that may also affect the type and/or amount of brain activity that is evoked from the user. For example, in scenario 100, the icons 104, 106, 108, 110 all have the same neutral color. Unlike the flicker rate, the icons 104, 106, 108, 110 may have the same or different colors as each other. The user interface may also have a particular background color. The background color may be the color of the HUD 102 or sections thereof. For example, in scenario 100, the HUD 102 is the same neutral color as the icons 104, 106, 108, 110 but with more transparency. The background color may be the same or different as the color of the icons 104, 106, 108, 110. Any or all of the foregoing display parameters of the HUD 102 and/or icons may be modified simultaneously or sequentially to affect brain activity.

Figure 2:
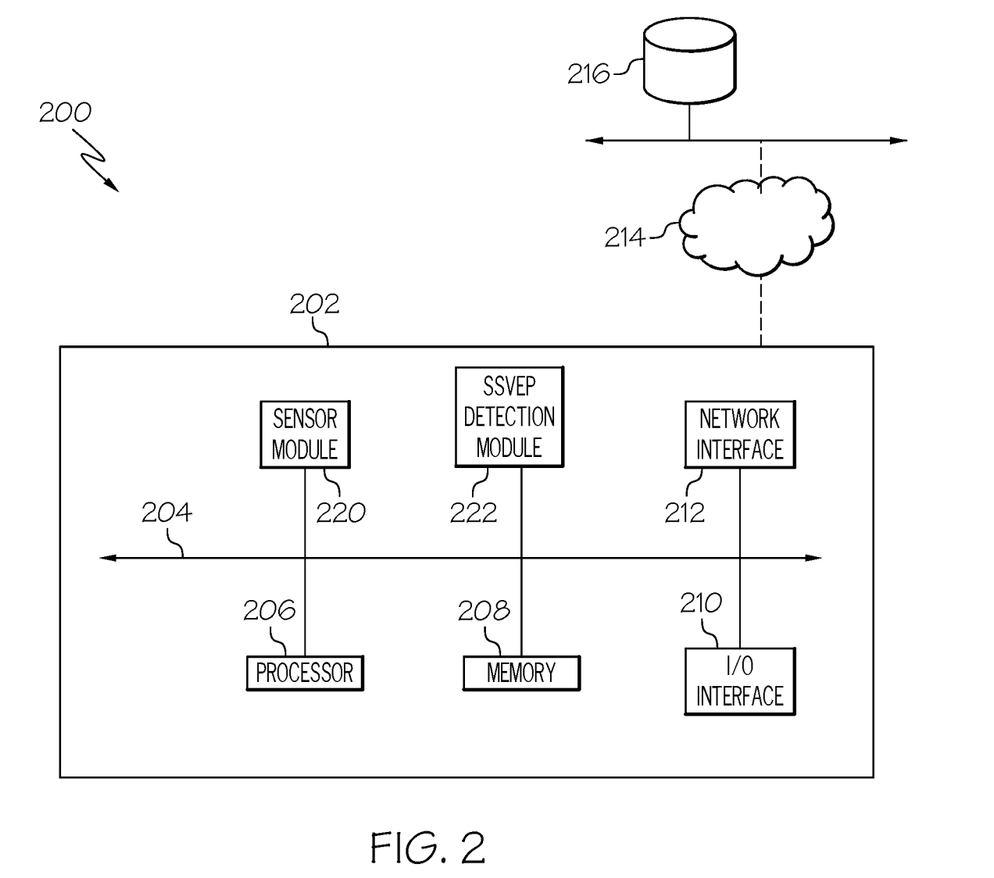
FIG. 2 schematically depicts an illustrative system for carrying out methods described herein, according to one or more embodiments shown and described herein.

Referring now to FIG. 2, a system 200 for carrying out methods described herein is schematically depicted. The system 200 may include a computing device 202 for executing the methods described herein. The computing device 202 may be a vehicle or part of a vehicle. The computing device 202 may comprise a processor 206, a memory module 208, a network interface 212, an input/output interface (I/O interface 210), a sensor module 220, and an SSVEP detection module 222. The computing device 202 also may include a communication path 204 that communicatively connects the various components of the computing device 202. The computing device 202 may connect to external computing devices 216 via a network 214. It should be understood that the components of the computing device 202 described are exemplary and may contain more or less than the number of components shown in FIG. 2.

The processor 206 may include one or more processors that may be any device capable of executing machine-readable and executable instructions. Accordingly, each of the one or more processors of the processor 206 may be a controller, an integrated circuit, a microchip, or any other computing device. The processor 206 is coupled to the communication path 204 that provides signal connectivity between the various components of the computing device 202. Accordingly, the communication path 204 may communicatively couple any number of processors of the processor 206 with one another and allow them to operate in a distributed computing environment. Specifically, each processor may operate as a node that may send and/or receive data. As used herein, the phrase "communicatively coupled" means that coupled components are capable of exchanging data signals with one another such as, e.g., electrical signals via a conductive medium, electromagnetic signals via air, optical signals via optical waveguides, and the like.

The communication path 204 may be formed from any medium that is capable of transmitting a signal such as, e.g., conductive wires, conductive traces, optical waveguides, and the like. In some embodiments, the communication path 204 may facilitate the transmission of wireless signals, such as Wi-Fi. Bluetooth, Near-Field Communication (NFC), and the like. Moreover, the communication path 204 may be formed from a combination of mediums capable of transmitting signals. In one embodiment, the communication path 204 comprises a combination of conductive traces, conductive wires, connectors, and buses that cooperate to permit the transmission of electrical data signals to components such as processors, memories, sensors, input devices, output devices, and communication devices. Additionally, it is noted that the term "signal" means a waveform (e.g., electrical, optical, magnetic, mechanical, or electromagnetic), such as DC, AC, sinusoidal-wave, triangular-wave, square-wave, vibration, and the like, capable of traveling through a medium.

The memory module 208 is communicatively coupled to the communication path 204 and may contain one or more memory modules comprising RAM, ROM, flash memories, hard drives, or any device capable of storing machine-readable and executable instructions such that the machine-readable and executable instructions can be accessed by the processor 206 The machine-readable and executable instructions may comprise logic or algorithms written in any programming language of any generation (e.g., 1GL, 2GL, 3GL, 4GL, or 5GL) such as, e.g., machine language, that may be directly executed by the processor, or assembly language, object-oriented languages, scripting languages, microcode, and the like, that may be compiled or assembled into machine-readable and executable instructions and stored on the memory module 208. Alternatively, the machine-readable and executable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components.

The I/O interface 210 is coupled to the communication path 204 and may contain hardware for receiving input and/or providing output. Hardware for receiving input may include devices that send information to the processor 206. For example, a keyboard, mouse, scanner, touchscreen, and camera are all I/O devices because they provide input to the processor 206. Hardware for providing output may include devices from which data is sent. For example, an electronic display, speaker, and printer are all I/O devices because they output data from the processor 206.

The sensor module 220 is coupled to the communication path 204 and communicatively coupled to the processor 206. The sensor module 220 may include sensors such as LiDAR sensors, RADAR sensors, optical sensors (e.g., cameras), laser sensors, proximity sensors, location sensors, and the like. The sensor module 220 may further include sensors for measuring brain activity such as electroencephalography (EEG) sensors. EEG sensors may include electrodes that may be in contact with a user and/or coils that may be in proximity to the user.

The computing device 202 also comprises the network interface 212. The network interface 212 is communicatively coupled to the communication path 204. The network interface 212 can be any device capable of transmitting and/or receiving data via a network or other communication mechanisms. Accordingly, the network interface 212 can include a communication transceiver for sending and/or receiving any wired or wireless communication. For example, the network interface 212 may include an antenna, a modem, an Ethernet port, a Wi-Fi card, a WiMAX card, a cellular modem, near-field communication hardware, satellite communication hardware, and/or any other wired or wireless hardware for communicating with other networks and/or devices. The network interface 212 communicatively connects the computing device 202 to external systems, such as external computing devices 216, via a network 214. The network 214 may be a wide area network, a local area network, a personal area network, a cellular network, a satellite network, and the like.

The system 200 may also include external computing devices 216. The external computing devices 216 may be one or more computing devices that may be in remote communication with the computing device 202 via network 214. The external computing devices 216 may include devices that operate beyond the computing device 202 such as desktop computers, laptop computers, smartphones, and any other type of computing device in communication with the computing device 202. The external computing devices 216 may also include services that operate beyond the computing device 202 that may be utilized by or may utilize the computing device 202, such as external databases, storage devices, computing platforms, and any other type of service.

The SSVEP detection module 222 may be a hardware module coupled to the communication path 204 and communicatively coupled to the processor 206. The SSVEP detection module 222 may also or instead be a set of instructions contained in the memory module 208. The SSVEP detection module 222 is configured to interact with an EEG sensor (e.g., sensor module 220) to measure brain activity for one or more frequencies and store and/or modify one or more display parameters of an electronic display (e.g., I/O interface 210). The SSVEP detection module 222 may also be configured to perform the methods as described herein, such as the methods as described in FIGS. 3 and 4.

It should be understood that the components illustrated in FIG. 2 are merely illustrative and are not intended to limit the scope of this disclosure. More specifically, while the components in FIG. 2 are illustrated as residing within computing device 202, this is a non-limiting example. In some embodiments, one or more of the components may reside external to computing device 202. In some embodiments, the computing device 202 may exist as a virtual machine operating within a host machine alongside other virtual machines, each of which shares the same computing resources belonging to the host machine.

Figure 3:
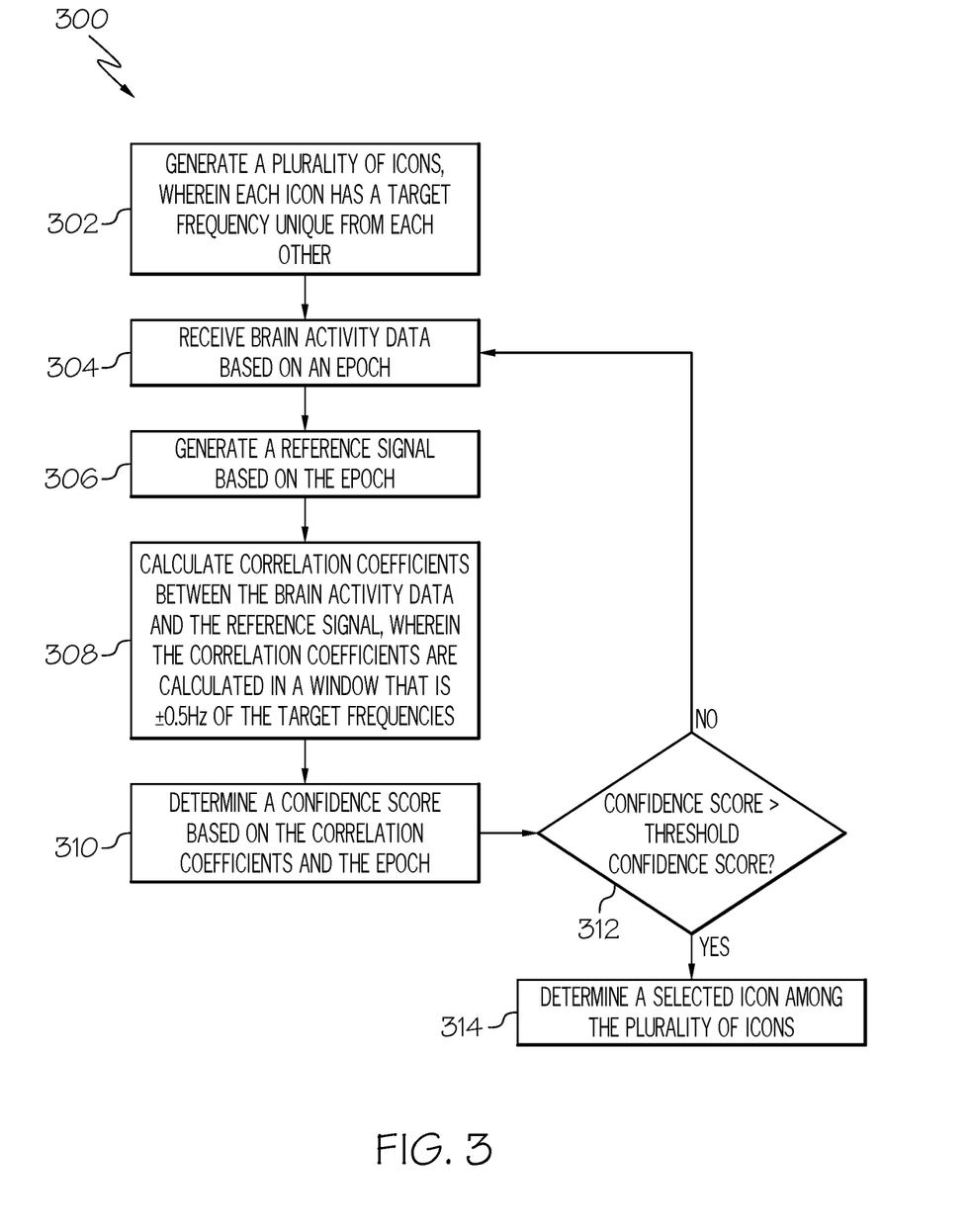
FIG. 3 depicts a flowchart of an illustrative method for SSVEP detection, according to one or more embodiments shown and described herein.

Referring now to FIG. 3, a flowchart of a method 300 for SSVEP detection is depicted. With reference to FIG. 2, the method 300 may be performed by the system 200, particularly with the SSVEP detection module 222. At block 302, the system 200 may generate a plurality of icons. The plurality of icons may be generated by the I/O interface 210 onto an electronic display. Each icon of the plurality of icons has a target frequency. Each target frequency may be unique and within an SSVEP frequency response range (e.g., 3.5 Hz to 75 Hz). For example, a first icon flickers at a target frequency of 10 Hz, which may evoke EEG signals in the user that are recorded by the system 200, while a second icon flickers at a target frequency of 12 Hz, Additionally, each target frequency may have multiple harmonic frequencies that are multiples of the target frequency.

At block 304, the system 200 may receive brain activity data. A user that views the electronic display having the plurality of icons may be in contact with or in communicative proximity to a brain activity sensor configured to gather brain activity data. For example, the sensor module 220 may have EEG electrodes that are in contact with the user or a wireless brain activity sensor built into a seat headrest positioned near the user's head such that the wireless brain activity sensor may detect the user's brain activity. In some embodiments, the brain activity data may be gathered by a sensor on an external computing device 216 and sent to the system 200 via network 214. The brain activity data is steady-state visually evoked potential (SSVEP) data generated by a user in response to the user viewing a visual stimulus, such as an icon of the plurality of icons.

The brain activity data may be sent to the SSVEP detection module 222 for processing. The SSVEP detection module 222 may process the brain activity data into a function having variables including frequency and power. For example, the SSVEP detection module 222 may apply a power spectral density estimate to the brain activity data to generate a line that represents the power for each frequency of the brain activity data. As another example, the SSVEP detection module 222 may calculate a Fast Fourier Transform to split the original brain activity into frequencies that can be classified by power.

The brain activity data may be sent to the SSVEP detection module 222 before, after, or during each epoch. An epoch, in terms of brain activity monitoring, is a time window in a brain activity (e.g., EEG) signal, which may be predetermined. For example, an epoch may be one second or less.

At block 306, the system 200 may generate a reference signal. The reference signal may be a synthetically generated reference signal having sine and/or cosine waves. The reference signal may have the same length as the brain activity data and may also be based on the same epoch duration. To generate the sine-cosine reference signal, the SSVEP detection module 222 may, for example, calculate:

$$\text{Reference} = \begin{bmatrix} \sin(2\pi f n) \\ \cos(2\pi f n) \\ \vdots \\ \sin(2\pi N_h f n) \\ \cos(2\pi N_h f n) \end{bmatrix}, n = \frac{1}{f_s}, \frac{2}{f_s}, \ldots, \frac{N}{f_s}$$

wherein $f$ is the target frequency, $f_s$ is the stimulus frequency, $N_h$ is the number of harmonics, and N is the number of sampling points.

At block 308, the system 200 may calculate correlation coefficients. Correlation coefficients may be calculated by performing a canonical correlation analysis (CCA) between brain activity data (e.g., EEG signals) and reference signals at target frequencies. The frequency of the reference signals with the maximal correlation is selected as the frequency of the brain activity data.

The purpose of calculating correlation coefficients is to determine the stimulating frequency from the brain activity data. Correlation coefficients may help determine the stimulating frequency because the flickering effect of an icon evokes brain activity (e.g., EEG) that has a higher canonical correlation with the reference signal at the stimulating frequency. Accordingly, the SSVEP detection module 222 may calculate correlation coefficients between the brain activity data and the reference signal. Rather than calculating correlation coefficients for each frequency between the brain activity data and the reference signal, however, the correlation coefficients are calculated in a window that is within ±0.5 Hz of the target frequencies, including the target frequencies and endpoints. Reducing the number of correlation coefficients that are calculated will improve the time it takes the SSVEP detection module 222 to determine the icon that the user is attempting to interact with. For example, the windows may be approximately ±0.5 Hz, ±0.4 Hz, ±0.3 Hz, ±0.2 Hz, or ±0.1 Hz of the target frequencies and/or harmonics thereof. However, the windows may also or instead by approximately ±0.7 Hz or ±0.6 Hz. for example, to further account for any imprecisions in the detection of brain wave activity or rounding in the processing of brainwave activity. Windows may have step size of approximately 0.1 Hz or smaller. It should be understood that frequency windows may or may not be of uniform size between frequencies and/or icons.

In some embodiments, the SSVEP detection module 222 may use the second harmonic frequency of a target frequency rather than the target frequency. This is because the second harmonic frequency may be stronger than the corresponding target frequency in some instances, and a stronger signal may provide more accurate results. Accordingly, the SSVEP detection module 222 may determine whether a second harmonic frequency of the target frequency is stronger than the target frequency for each target frequency based on the brain activity data. If the second harmonic frequency is stronger than its corresponding target frequency, the SSVEP detection module 222 may calculate correlation coefficients in a window that is within ±0.5 Hz of the second harmonic frequency.

At block 310, the system 200 may determine a confidence score. Brain activity data may be continuously acquired, as in block 304, based on a predetermined epoch (e.g., 0.5 seconds). in some embodiments, the epoch may be set based on a predetermined length of time that the user must focus on an icon to make a selection. For each epoch, the system 200 may also continue to perform blocks 306. After each epoch, the epoch may receive a confidence score based on the correlation coefficients calculated in block 308. For example, the confidence score of an epoch may be the strength of the strongest target frequency or based on a formula wherein the frequencies having the highest correlation coefficient are assigned a confidence score of the correlation coefficient weighted by the strength of the frequency. The scoring metric may also or instead be based on a plurality of past epochs. For example, the confidence score of an epoch may be the highest of a running total or moving average of the past three (or any other number) scores for each target frequency.

At block 312, the system 200 may determine whether the confidence score surpasses a threshold confidence score. The threshold confidence score may be predetermined or calculated. A calculated threshold confidence score may be determined based on a desired level of sensitivity. For example, the SSVEP-based BCI may have configurations that allow it to be more or less sensitive as the user desires, where more sensitivity may be attributed to a lower confidence threshold. After a confidence score is calculated in block 310, if the confidence score does not surpass the threshold confidence score, then the system 200 may continue to perform blocks 304, 306, 308, 310 until the confidence score surpasses the threshold confidence score. Once the confidence score surpasses the threshold confidence score, the system 200 may proceed to block 314.

At block 314, the system 200 may determine a selected icon among the plurality of icons. Determining a selected icon may be based on the correlation coefficients and in response to the confidence score surpassing the threshold confidence score in block 312. For example, if the confidence score threshold is 75% (or any other number), the selected icon may be the icon having a target frequency with the highest correlation coefficient for the past three out of four consecutive epochs. Additionally or alternatively, determining a selected icon may be based on the confidence score and in response to the confidence score surpassing the threshold confidence score in block 312. For example, the selected icon may be the icon having a target frequency with the highest correlation coefficient when the confidence score is surpassed. Once the selected icon is determined, the system 200 may react by outputting a control signal based on the selected icon. For example, if a "power off" icon is determined to have been interacted with by the user, then the system 200 may output a control signal to the processor 206 to power off the system 200.

Machine-readable instructions for performing method 300 may be represented by the following pseudocode:

```
FOR EACH second IN [seconds]:
  t:=accumulative time of experiment
  n:=sample rate
  m:=#of channels
  f:=#of target frequencies
  SSVEP:=real-time from EEG sensor for t seconds as
    m×[n×t] matrix
  threshold:=0.6
  FOR EACH target frequency IN target frequencies:
    reference signals:=build reference signal for ±0.5 Hz
      target frequency and second harmonic frequency of
      target
    frequency as 4×[n×t] matrix
  FOR EACH reference signal in reference signals:
    CCs+=calculate CCAs for target frequency as 4×1
      matrix
  FOR EACH CC IN CCs
    CC_sums+=sum of 4×1 matrix CC
    max_CC:=maximum of CC_sums
``` max_CC_freq:=target frequency of target frequencies having max_cc
accuracies:=[number of selection/t] as $f \times 1$ matrix
IF t<10:
   FOR accuracy IN accuracies:
      IF accuracy>threshold:
         select final frequency
      ELSE:
         keep recording
ELSE
   end without selection.

Figure 4:
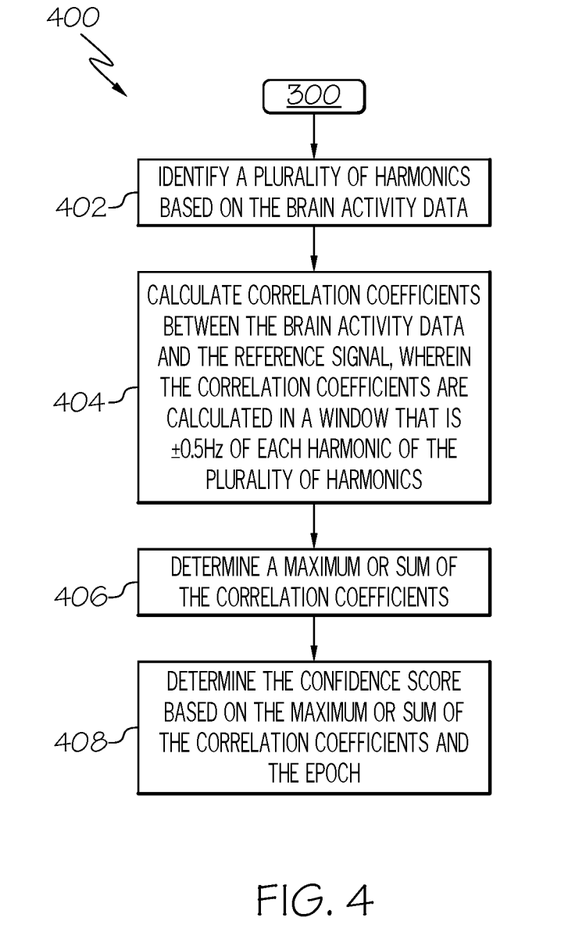
FIG. 4 depicts a flowchart of an illustrative method for determining a confidence score based on correlation coefficients, according to one or more embodiments shown and described herein.

Referring now to FIG. 4, a flowchart of a method 400 for determining a confidence score based on correlation coefficients is depicted. With reference to FIGS. 2 and 3, the method 400 may be performed by the system 200, particularly with the SSVEP detection module 222. The method 400 represents an additional embodiment of the method 300, wherein the harmonic frequencies of the target frequencies may be used in addition to or instead of the target frequencies in determining a confidence score. Accordingly, in block 402, the system 200 may identify a plurality of harmonic frequencies. The harmonic frequencies may be multiples of the target frequencies. For example, if an icon has a target frequency of 10 Hz, then its harmonic frequencies may be 20 Hz, 30 Hz, and so on.

In block 404, the system 200 may calculate correlation coefficients. The purpose of calculating correlation coefficients is to determine the stimulating frequency. This is because the flickering effect of an icon evokes brain activity that has a higher canonical correlation with the reference signal at the stimulating frequency. Accordingly, the SSVEP detection module 222 may calculate correlation coefficients between the brain activity data and the reference signal of block 306. The frequency of the reference signals with the maximal correlation is selected as the frequency of the brain activity data.

Rather than calculating correlation coefficients for each frequency between the brain activity data and the reference signal, however, the correlation coefficients are calculated in a window that is within ±0.5 Hz of the identified harmonic frequencies of block 402, including the harmonic frequencies as well as endpoints. Reducing the number of correlation coefficients that are calculated will improve the time it takes the SSVEP detection module 222 to determine the icon that the user is attempting to interact with. Compared to block 308, block 404 may only increase the computational overhead of the method 400 in that it performs calculations for one or more harmonic frequencies rather than a single target frequency. The method 400 is still faster than traditional methods because it reduces the number of correlation coefficients that are calculated which will improve the time it takes the SSVEP detection module 222 to determine the icon that the user is attempting to interact with.

In block 406, the system 200 may determine a maximum and/or a sum of the correlation coefficients for calculating determining a confidence score of an epoch. If the system 200 is configured to score an epoch by its maximum correlation coefficient, the system 200 may determine the highest valued correlation coefficients of the target frequency and harmonic frequencies thereof for one or more icons. For instance, the correlation coefficients may be the highest at the target frequency for a first icon but highest at the second harmonic frequency for a second icon. The confidence level in block 408, therefore, may then be a function having the variables of the maximum correlation coefficients for one or more icons. The function that is the confidence level may also have variables including the strength of the frequency having the highest valued correlation coefficient for one or more icons. To determine the strength of a frequency, the SSVEP detection module 222 may process the brain activity data into a function with variables including frequency and power based on the correlation coefficients and reference signal. For example, the SSVEP detection module 222 may apply a power spectral density estimate to the brain activity data to generate a line that represents power for each frequency of the brain activity data. A frequency may be considered stronger than another if it has more power in the brain activity data.

Referring back to block 406, if the system 200 is configured to score an epoch by the sum of its correlation coefficients, the system 200 may determine a sum of the correlation coefficients by summing the correlation coefficient of the target frequency and/or one or more corresponding harmonic frequencies for each icon. For instance, a first icon and a second icon may each have one or more correlation coefficients that may be summed between (e.g., target frequencies of the first icon and the second icon) and/or among (e.g., target frequencies and harmonic frequencies thereof of each icon) icons. The confidence level in block 408, therefore, may then be a function having the variables of the sum of the correlation coefficients of each icon and/or the sum of all correlation coefficients. The function that is the confidence level may also have variables including the strength of the target and/or harmonic frequency.

After the method 400 has been completed for an epoch, the system 200 may proceed with the method 300 at block 312, where the confidence score may be compared against a threshold confidence score.

Figure 5:
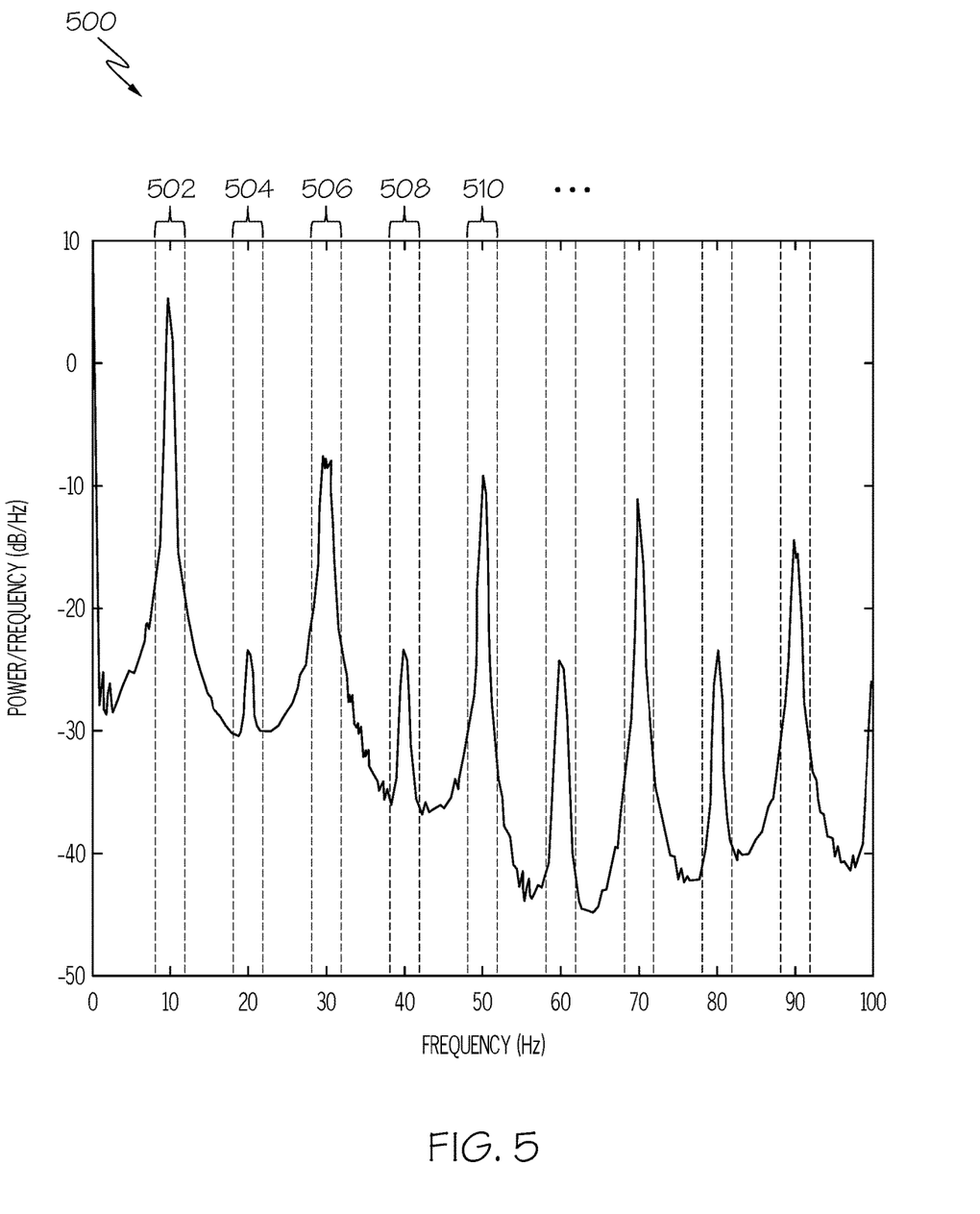
FIG. 5 depicts an illustrative power spectral density analysis of the 10 Hz frequency, according to one or more embodiments shown and described herein.

Referring now to FIG. 5, a power spectral density analysis (PSD analysis 500) of the 10 Hz frequency is depicted. Particularly, the PSD analysis 500 depicts the brain activity of a user in response to viewing an icon flickering at a target frequency of 10 Hz with a 50% duty cycle for one epoch. The PSD analysis 500 may be generated by any method for generating a PSD analysis, such as Welch's method. To generate the PSD analysis 500, a system may receive brain activity data from a user viewing a visual stimulus, in this case an icon flickering at 10 Hz with a 50% duty cycle. Brain activity sensors (e.g., electrodes) on or near the user collect the brain activity data to send to the system, wherein the system applies a power spectral density estimate to create the PSD analysis 500. The system may generate a PSD analysis for each icon.

After receiving the PSD analysis 500, the system may determine one or more frequency windows in which the system will perform the remaining steps for determining which icon has been selected. For example, the system may determine frequency windows 502, 504, 506, 508, 510. Limiting further analysis to the frequency windows improves the speed of the BCI because it reduces the number of calculations the system must perform per epoch to subsets of the brain activity data rather than the entire brain activity data. For example, if the target frequency and second harmonic frequency are to be analyzed, the system may only need to analyze 9.5 Hz-10.5 Hz and 19.5 Hz-20.5 Hz rather than 0 Hz-100 Hz. A frequency window may be ±0.5 Hz of the target frequency and/or one or more harmonic frequencies thereof. For example, ±0.5 Hz of the target frequency 10 Hz is frequency window 502, ±0.5 Hz of the second harmonic frequency 20 Hz is frequency window 504, ±0.5 Hz of the third harmonic frequency 30 Hz is frequency window 506, and so on. Similarly, when generating a reference signal and calculating correlation coefficients, the system may only perform the generating and calculating for the frequency windows 502, 504, 506, 508, 510.

After each epoch, the system may calculate a confidence score for the epoch based on the calculated correlation coefficients. The confidence score may be based on the value of the correlation coefficient in one or more frequency windows and/or strength of the signal in one or more frequency windows. For example, if the frequency window 502 of the PSD analysis 500 has the strongest signal strength as compared to the PSD analyses of the other displayed icons at their respective target frequencies, then the epoch of the PSD analysis 500 may have a confidence score commensurate to the strength of the strongest frequency of the PSD analysis 500 (e.g., frequency window 502). The confidence score may also or instead be based on a formula wherein the frequency windows having the highest value correlation coefficient are assigned a confidence score weighted by the value of the correlation coefficient and/or strength of the frequency. In some embodiments, the confidence score may also or instead be based on a plurality of past epochs, For example, the confidence score of an epoch may be the highest of a running total or moving average of the past three (or any other number) scores for each PSD analysis.

After calculating the confidence score, the system may determine whether the confidence score surpasses a threshold confidence score. The threshold confidence score may be predetermined or calculated. For example, the system may have a predetermined confidence threshold of 80%, wherein the threshold is met when the past 4 out of 5 epochs had the strongest signal at frequency window 502. A calculated threshold confidence score may be determined based on a desired level of sensitivity. For example, a system may have a user-configurable sensitivity level of high, medium, and low, wherein a high sensitivity may correspond to a low threshold confidence score, a medium sensitivity may correspond to a medium threshold confidence score, and a low sensitivity corresponds to a high threshold confidence score. In some embodiments, the threshold confidence score may also be a function of a threshold signal strength to prevent accidental selection when the user is not focused on any icon.

After a confidence score is calculated, if the confidence score does not surpass the threshold confidence score, then the system may continue to analyze brain activity data, calculate correlation coefficients, and calculate confidence scores until the confidence score surpasses the threshold confidence score. Once the confidence score surpasses the threshold confidence score, the system may determine a selected icon among the plurality of icons. Determining a selected icon may be based on the correlation coefficients and in response to the confidence score surpassing the threshold confidence score. For example, if the confidence score threshold is 75% (or any other number), the selected icon may be the icon having a target frequency with the highest correlation coefficient for the past three out of four consecutive epochs. Additionally or alternatively, determining a selected icon may be based on the confidence score and in response to the confidence score surpassing the threshold confidence score, For example, the selected icon may be the icon having a target frequency with the highest correlation coefficient when the confidence score is surpassed. Once the selected icon is determined, the system may react by outputting a control signal based on the selected icon.

Figure 6:
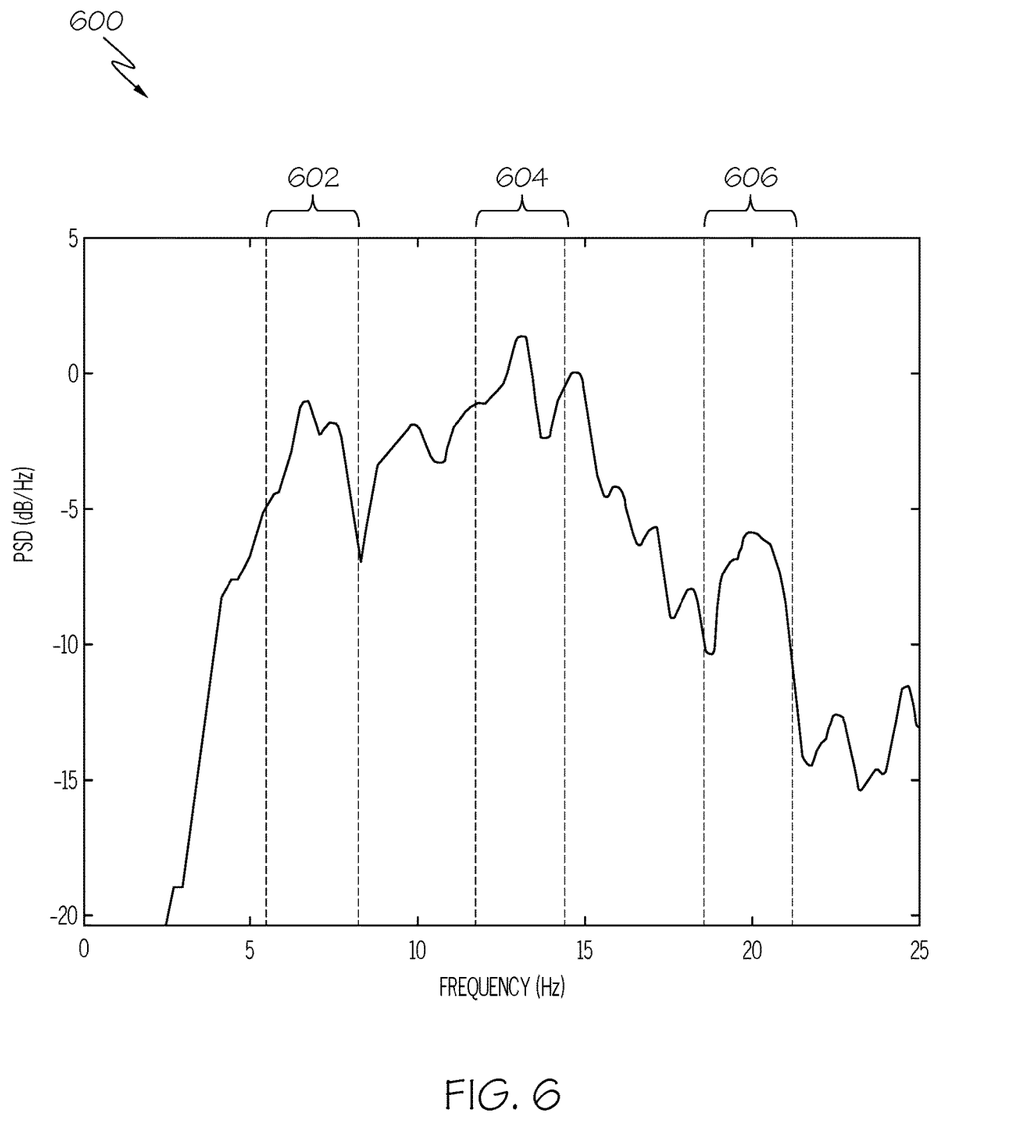
FIG. 6 depicts an illustrative power spectral density analysis of the 6.67 Hz frequency, according to one or more embodiments shown and described herein.

Referring now to FIG. 6, a PSD analysis 600 of the 6.67 Hz frequency is depicted. Particularly, the PSD analysis 600 depicts the brain activity of a user in response to viewing an icon flickering at a target frequency of 6.67 Hz with a 50% duty cycle for one epoch. Unlike the PSD analysis 500 of FIG. 5, the PSD analysis 600 has a stronger second harmonic frequency than the target frequency. The PSD analysis 600 may be generated by any method for generating a PSD analysis, such as Welch's method. To generate the PSD analysis 600, a system may receive brain activity data from a user viewing a visual stimulus, in this case an icon flickering at 6.67 Hz with a 50% duty cycle. Brain activity sensors (e.g., electrodes) on or near the user collect the brain activity data to send to the system, wherein the system applies a power spectral density estimate to create the PSD analysis 600. The system may generate a PSD analysis for each icon.

After receiving the PSD analysis 600, the system may determine one or more frequency windows in which the system will perform the remaining steps for determining which icon has been selected. For example, the system may determine frequency windows 602, 604, 606. Limiting further analysis to the frequency windows improves the speed of the BCI because it reduces the number of calculations the system must perform per epoch to subsets of the brain activity data rather than the entire brain activity data. A frequency window may be ±0.5 Hz of the target frequency and/or one or more harmonic frequencies thereof. For example, ±0.5 Hz of the target frequency 6.67 Hz is frequency window 602, ±0.5 Hz of the second harmonic frequency 13.34 Hz is frequency window 604, ±0.5 Hz of the third harmonic frequency 20 Hz is frequency window 606, and so on. Similarly, when generating a reference signal and calculating correlation coefficients, the system may only perform the generating and calculating for the frequency windows 602, 604, 606, However, in some embodiments, the frequencies analyzed may be further narrowed to the strongest frequency window of a PSD analysis. That is, the system may use the stronger of the target frequency or a harmonic frequency of the target frequency in calculating a correlation coefficient for an icon. A harmonic frequency of a target frequency may be considered stronger than the target frequency if it has more power in the brain activity data than its corresponding target frequency. For example in PSD analysis 600, the second harmonic frequency (i.e., 13.34 Hz) is stronger than the target frequency (i.e., 6.67 Hz) because the second harmonic frequency has a strength higher than 0 dB/Hz whereas the target frequency has a strength lower than 0 dB/Hz, and thus the frequency window 604 may be used for calculating correlation coefficients.

After each epoch, the system may calculate a confidence score for the epoch based on the calculated correlation coefficients. The confidence score may be based on the strength of the correlation coefficient and/or strength of the signal in the frequency window. For example, if the frequency window 602 of the PSD analysis 600 has the strongest signal strength as compared to the PSD analyses of the other displayed icons at their respective target frequencies, then the epoch of the PSD analysis 600 may have a confidence score commensurate to the strength of the strongest frequency of the PSD analysis 600 (e.g., frequency window 604). The confidence score may also or instead be based on a formula wherein the frequency windows having the highest correlation coefficient are assigned a confidence score weighted by the strength of the correlation coefficient, strength of the frequency, and/or or difference between the strength of the strongest frequency of PSD analysis 600 and the strength of the strongest frequencies of the PSD analyses for previous epochs. In some embodiments, the confidence score may also or instead be based on a plurality of past epochs. For example, the confidence score of an epoch may be the highest of a running total or moving average of the past three (or any other number) scores for each PSD analysis.

In some embodiments, the system may be configured to score an epoch by its maximum correlation coefficient, wherein the system may determine the highest valued correlation coefficients of the target frequency and harmonic frequencies thereof for each icon. For instance, the correlation coefficients may be the highest at the target frequency for a first icon but highest at the second harmonic frequency for a second icon as shown in PSD analysis 600 at frequency window 604. The confidence level, therefore, may then be a function having the variables of the maximum correlation coefficients for one or more icons. The function that is the confidence level may also have variables including the strength of the frequency having the valued correlation coefficient for an icon.

In other embodiments, the system may be configured to score an epoch by the sum of its correlation coefficients, wherein the system may determine a sum of the correlation coefficients by summing the correlation coefficient of the target frequency and/or one or more corresponding harmonic frequencies for each icon. The confidence level, therefore, may then be a function having the variables of the sum of all or some correlation coefficients of each icon and/or the sum of all correlation coefficients between icons. The function that is the confidence level may also have variables including the strength of the frequency having the valued correlation coefficient for an icon.

After calculating the confidence score, the system may determine whether the confidence score surpasses a threshold confidence score. The threshold confidence score may be predetermined or calculated. For example, the system may have a predetermined confidence threshold of 80%, wherein the threshold is met when the past 4 out of 5 epochs had the strongest signal at frequency window 604. A calculated threshold confidence score may be determined based on a desired level of sensitivity. For example, a system may have a user-configurable sensitivity level of high, medium, and low, wherein a high sensitivity may correspond to a low threshold confidence score, a medium sensitivity may correspond to a medium threshold confidence score, and a low sensitivity corresponds to a high threshold confidence score. In some embodiments, the threshold confidence score may also be a function of a threshold signal strength to prevent accidental selection when the user is not focused on any icon.

After a confidence score is calculated, if the confidence score does not surpass the threshold confidence score, then the system may continue to analyze brain activity data, calculate correlation coefficients, and calculate confidence scores until the confidence score surpasses the threshold confidence score. Once the confidence score surpasses the threshold confidence score, the system may determine a selected icon among the plurality of icons. Determining a selected icon may be based on the correlation coefficients and in response to the confidence score surpassing the threshold confidence score. Additionally or alternatively, determining a selected icon may be based on the confidence score and in response to the confidence score surpassing the threshold confidence score. Once the selected icon is determined, the system may react by outputting a control signal based on the selected icon.

It should now be understood that disclosed herein are embodiments methods, systems, and non-transitory computer-readable mediums having machine-readable instructions for SSVEP detection. An SSVEP-based BCI may utilize an electronic display to present a user interface to a user. The user interface may have a plurality of flickering icons that invoke brain activity in a user when the user views an icon. The SSVEP-based BCI may utilize CCA to determine the icon the user is viewing. CCA calculates the correlation coefficients between two datasets: the acquired brain activity (e.g., EEG) data from the BCI user and a synthetically generated sine-cosine reference signal. Target frequencies are identified based on the correlation coefficients between the two datasets for each frequency of the reference signal. Embodiments reduce the time and resources needed to identify the stimulating frequency by narrowing the analysis to the target frequencies and/or one or more corresponding harmonic frequencies as well as a window of ±0.5 Hz to account for imprecisions that naturally occur in the SSVEP paradigm. In addition, embodiments continue to calculate correlation coefficients based on an epoch until it reaches a pre-defined confidence score threshold. The confidence score may be based on one or more confidence scores (e.g., maximum, total, average, etc.) of one or more epochs (e.g., the previous epoch, a running total of epochs, or a moving average of epochs). Once the confidence score threshold is met, the selected icon may be determined based on the correlation coefficients of one or more epochs.

For the purposes of describing and defining the present disclosure, it is noted that reference herein to a variable being a "function" of a parameter or another variable is not intended to denote that the variable is exclusively a function of the listed parameter or variable. Rather, reference herein to a variable that is a "function" of a listed parameter is intended to be open-ended such that the variable may be a function of a single parameter or a plurality of parameters.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

What is claimed is:

1. A method comprising:
   generating a plurality of icons, wherein each icon has a target frequency unique from each other;
   receiving brain activity data based on an epoch;
   generating a reference signal based on the epoch;
   calculating correlation coefficients between the brain activity data and the reference signal, wherein the correlation coefficients are calculated in a window that is within ±0.5 Hz of the target frequencies, including endpoints;
   determining a confidence score based on the correlation coefficients and the epoch; and
   determining a selected icon among the plurality of icons based on the correlation coefficients in response to the confidence score surpassing a threshold confidence score.

2. The method of claim 1, wherein the brain activity data is steady-state visually evoked potential (SSVEP) data generated by a user in response to the user viewing the plurality of icons.

3. The method of claim 1, further comprising determining, for each target frequency based on the brain activity data, whether a harmonic frequency of the target frequency is stronger than the target frequency.

4. The method of claim 3, wherein the correlation coefficients are also calculated in a window that is within ±0.5 Hz of the harmonic frequency of the target frequency for each target frequency that is not stronger than the harmonic frequency of the target frequency.

5. The method of claim 1, further comprising:
   identifying a plurality of harmonic frequencies based on the target frequencies; and
   calculating correlation coefficients between the brain activity data and the reference signal, wherein the correlation coefficients are calculated in a window that is within ±0.5 Hz of each harmonic frequency of the plurality of harmonic frequencies, including endpoints.

6. The method of claim 5, wherein determining the confidence score based on the correlation coefficients and the epoch comprises:
   determining a maximum correlation coefficient of the correlation coefficients; and
   determining the confidence score based on the maximum correlation coefficient and the epoch.

7. The method of claim 5, wherein determining the confidence score based on the correlation coefficients and the epoch comprises:
   determining a sum of the correlation coefficients; and
   determining the confidence score based on the sum of the correlation coefficients and the epoch.

8. The method of claim 1, further comprising outputting a control signal based on the selected icon.

9. A system comprising:
   a processor;
   an electronic display;
   a brain activity sensor; and
   a memory module having machine-readable instructions that, when executed by the processor, cause the processor to perform operations comprising:
      generating a plurality of icons, wherein each icon has a target frequency unique from each other;
      receiving brain activity data based on an epoch;
      generating a reference signal based on the epoch;
      calculating correlation coefficients between the brain activity data and the reference signal, wherein the correlation coefficients are calculated in a window that is within ±0.5 Hz of the target frequencies, including endpoints;
      determining a confidence score based on the correlation coefficients and the epoch; and
      determining a selected icon among the plurality of icons based on the correlation coefficients in response to the confidence score surpassing a threshold confidence score.

10. The system of claim 9, wherein the brain activity data is steady-state visually evoked potential (SSVEP) data generated by a user in response to the user viewing the plurality of icons.

11. The system of claim 9, wherein the machine-readable instructions, when executed by the processor, cause the processor to perform operations further comprising determining, for each target frequency based on the brain activity data, whether a harmonic frequency of the target frequency is stronger than the target frequency.

12. The system of claim 11, wherein the correlation coefficients are also calculated in a. window that is within ±0.5 Hz of the harmonic frequency of the target frequency for each target frequency that is not stronger than the harmonic frequency of the target frequency.

13. The system of claim 9, wherein the machine-readable instructions, when executed by the processor, cause the processor to perform operations further comprising:
    identifying a plurality of harmonic frequencies based on the target frequencies; and
    calculating correlation coefficients between the brain activity data and the reference signal, wherein the correlation coefficients are calculated in a window that is within ±0.5 Hz of each harmonic frequency of the plurality of harmonic frequencies, including endpoints.

14. The system of claim 13, wherein determining the confidence score based on the correlation coefficients and the epoch comprises:
    determining a maximum correlation coefficient of the correlation coefficients; and
    determining the confidence score based on the maximum correlation coefficient and the epoch.

15. The system of claim 13, wherein determining the confidence score based on the correlation coefficients and the epoch comprises:
    determining a sum of the correlation coefficients; and
    determining the confidence score based on the sum of the correlation coefficients and the epoch.

16. The system of claim 9, wherein the machine-readable instructions, when executed by the processor, cause the processor to perform operations further comprising outputting a control signal based on the selected icon.

17. A non-transitory computer-readable medium having machine-readable instructions that, when executed by a processor, cause the processor to perform operations comprising:
    generating a plurality of icons, wherein each icon has a target frequency unique from each other;
    receiving brain activity data based on an epoch;
    generating a reference signal based on the epoch;
    calculating correlation coefficients between the brain activity data and the reference signal, wherein the correlation coefficients are calculated in a window that is within ±0.5 Hz of the target frequencies, including endpoints;

determining a confidence score based on the correlation coefficients and the epoch; and determining a selected icon among the plurality of icons based on the correlation coefficients in response to the confidence score surpassing a threshold confidence score.

18. The non-transitory computer-readable medium of claim 17, wherein the machine-readable instructions, when executed by the processor, cause the processor to perform operations further comprising:

identifying a plurality of harmonic frequencies based on the target frequencies; and calculating correlation coefficients between the brain activity data and the reference signal, wherein the correlation coefficients are calculated in a window that is within ±0.5 Hz of each harmonic frequency of the plurality of harmonic frequencies, including endpoints.

19. The non-transitory computer-readable medium of claim 18, wherein determining the confidence score based on the correlation coefficients and the epoch comprises:

determining a maximum correlation coefficient of the correlation coefficients; and determining the confidence score based on the maximum correlation coefficient and the epoch.

20. The non-transitory computer-readable medium of claim 18, wherein determining the confidence score based on the correlation coefficients and the epoch comprises:

determining a sum of the correlation coefficients; and determining the confidence score based on the sum of the correlation coefficients and the epoch.

* * * * *

UNITED STATES PATENT AND TRADEMARK OFFICE
CERTIFICATE OF CORRECTION

| | |
|---|---|
| PATENT NO. | : 11,684,301 B1 |
| APPLICATION NO. | : 17/576370 |
| DATED | : June 27, 2023 |
| INVENTOR(S) | : Insoo Kim et al. |

It is certified that error appears in the above-identified patent and that said Letters Patent is hereby corrected as shown below:

On the Title Page

Item (71), applicant 2, insert --University of Connecticut Health Center, Farmington, CT (US)--.

In the Specification

In Column 6, Line(s) 26, after "12 Hz", delete "," and insert --.--, therefore.

In Column 8, Line(s) 65, after "CCs", insert --:--.

In Column 9, Line(s) 10, after "ELSE", insert --:--.

In Column 11, Line(s) 21, after "epochs", delete "," and insert --.--, therefore.

In Column 12, Line(s) 63, after "and/or", delete "or".

In the Claims

In Column 16, Line(s) 24, Claim 12, after "calculated in a", delete ".".

Signed and Sealed this
Twelfth Day of September, 2023

Katherine Kelly Vidal
*Director of the United States Patent and Trademark Office*